United States Patent [19]

Gurtovoi et al.

[11] 3,983,871
[45] Oct. 5, 1976

[54] APPARATUS FOR DIRECT BLOOD TRANSFUSION

[76] Inventors: Isaak Mordkovich Gurtovoi, ulitsa Pavla Dybenko, 4, kv. 42; Mark Isaakovich Gurtovoi, ulitsa Korolenko, 18, kv. 10; Evgeny Nikolaevich Khlopkov, ulitsa Serafimovicha, 28, kv. 32, all of Sevastopol, U.S.S.R.

[22] Filed: May 14, 1975

[21] Appl. No.: 577,465

[52] U.S. Cl. ............................ 128/214 B; 128/214.2; 417/148
[51] Int. Cl.² .......................................... A61M 1/02
[58] Field of Search ........ 128/214 R, 214 A, 214 B, 128/214 Z, 276; 417/148

[56] References Cited
UNITED STATES PATENTS

| | | | |
|---|---|---|---|
| 1,481,794 | 1/1924 | Dupin | 128/214 B |
| 1,696,496 | 12/1928 | McMurdo | 417/148 |
| 1,937,566 | 12/1933 | Hanafin et al. | 417/148 |
| 2,077,774 | 4/1937 | Rudder | 128/214 B |
| 2,625,932 | 1/1953 | Salisbury | 128/214 Z |
| 2,625,933 | 1/1953 | Salisbury | 128/214 Z |

*Primary Examiner*—Dalton L. Truluck
*Attorney, Agent, or Firm*—Holman & Stern

[57] ABSTRACT

An apparatus for direct blood transfusion which comprises two needles with tubes connected thereto. One needle is introduced into the donor's blood system, while the other into the recipient's blood system. In order to provide for the delivery of blood from the donor to the recipient via said tubes, the apparatus is equipped with a vessel containing a medicamental liquid compatible with blood and mounted at a height sufficient for creating a hydrostatic head of the medicamental liquid exceeding the blood pressure in the recipient's vasculature. The apparatus also comprises a distributing means built around at least four proportioning vessels vertically mounted in a housing and rigidly coupled therewith. The housing is disposed between the upper and lower disks of a stator in coaxial relationship therewith. The housing is made rotatable in one direction with respect to the stator. The upper disk and the lower disk of the stator each have at least four holes formed therein. As the housing turns, each of the proportioning vessels passes successively through at least four positions. In each position each proportioning vessel is so disposed with respect to the stator that its inlet and outlet register with said holes formed in the stator disks, so that the proportioning vessel occupying the first position has its inlet communicating with the tube connected to the needle introduced into the donor's blood system. The outlet of this proportioning vessel communicates with the air cushion in the vessel with the medicamental liquid. The proportioning vessel occupying the second position has its outlet communicating with the tube connected to the needle introduced into the recipient's blood system. The proportioning vessel occupying the third position has its inlet communicating with the vessel with the medicamental liquid. The outlet of this vessel and the inlet of the proportioning vessel occupying the second position communicate one with the other with the aid of a two-way cock which serves either to connect the foregoing vessels or else to connect the vessel with the medicamental liquid and the proportioning occupying the second position. The proportioning vessel occupying the fourth position has its inlet communicating with the atmosphere and its outlet with the vessel for the spent medicamental liquid.

4 Claims, 5 Drawing Figures

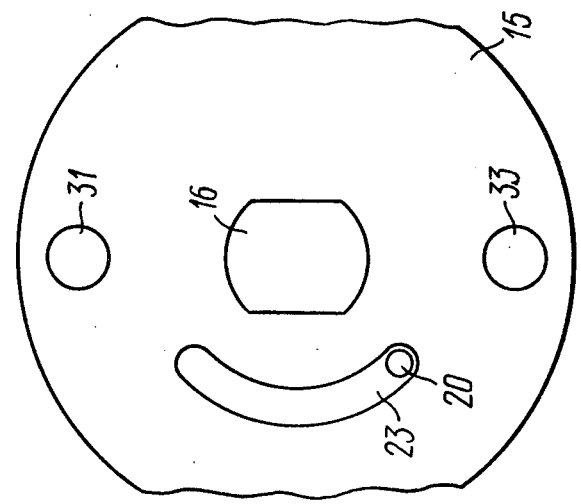
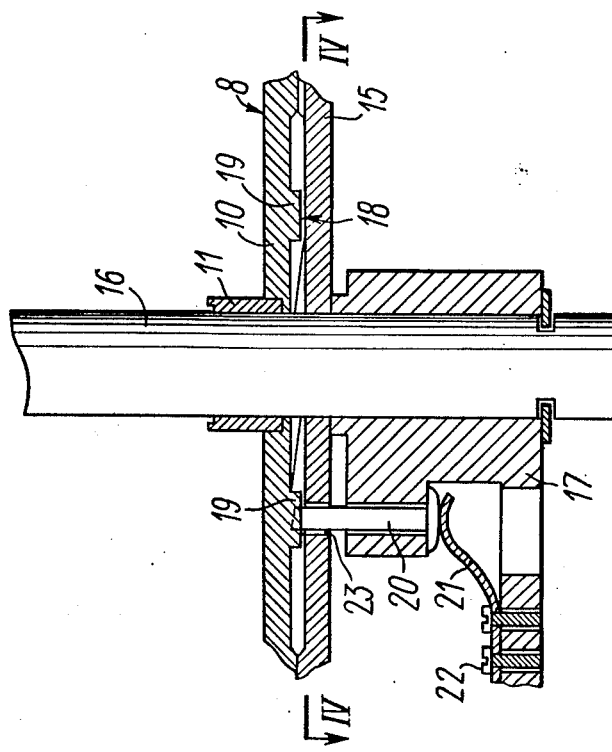

APPARATUS FOR DIRECT BLOOD TRANSFUSION

BACKGROUND OF THE INVENTION

The present invention relates to medical equipment, and, more particularly, to an apparatus for direct blood transfusion.

The apparatus of the present invention may be advantageously employed for direct blood transfusion as well as for introducing various medicamental liquids into the recipient's blood system.

There exist a variety of widely known apparatus for direct blood transfusion which usually comprise two needles coupled with tubes, one needle being introduced into the donor's blood system, while the other into the recipient's blood system, as well as a means for delivering blood from the donor to the recipient via said tubes. In order to prevent or combat blood clotting in the tubes, the latter must be regularly washed. To this end, the known apparatus are provided with a vessel (or several vessels) containing a medicamental liquid compatible with blood. The known apparatus also incorporate a distributing means, usually formed as a cock, which communicates with the above-described tubes as well as with the vessel containing the medicamental liquid. When the distributing means is set to one position, blood is delivered via the tubes from the donor to the recipient; with the distributing means set to the other position, said tubes undergo washing.

Blood is delivered from the donor to the recipient with the aid of a wide variety of pumps, such as centrifugal pumps, simplex, duplex and triplex pumps, reciprocating squirt pumps, plunger-type pumps, diaphragm pumps with a hydraulic drive, pumps with a monolithic compression plate, air-driven peristaltic pumps, gas-driven diaphragm pumps, pumps with a monolithic compression and flexible plate, etc.

From among the known apparatus for direct blood transfusion, the most popular variety uses the principle of continuous pumping of blood from the donor to the recipient, Beck's apparatus being the most widely known unit of this category.

This prior art apparatus comprises two needles coupled to rubber tubes. One needle is introduced into the blood system of the donor, the other into the blood system of the recipient. The above rubber tubes are interconnected by means of a glass tube affording a means of visual inspection of the transfusion process. The apparatus also incorporates a means for delivering blood from the donor to the recipient via the above-mentioned tubes, which means is formed as a drum with rollers disposed thereon.

In order to periodically wash the tubes with a view to preventing or combatting clotting therewithin, the apparatus is provided with a vessel containing a medicamental liquid compatible with blood. Additional tubes similar to the above-described ones have their free ends immersed in the vessel with the medicamental liquid, said additional tubes as well as the tubes connected to the needles which are introduced into the blood systems of the donor and the recipient being disposed on said drum.

The apparatus further comprises a distributing means in the form of a two-way cock communicating with said tubes as well as with the vessel for the medicamental liquid. The cock is mounted between the rubber tube connected to the needle introduced into the donor's blood system and one of the rubber tubes immersed in the vessel with the medicamental liquid.

With the cock set to one position, as the drum rotates, in one direction, the rollers run on the rubber tubes connected to the donor's and recipient's needles. Where the rollers come into contact with the tubes, the latter are deformed, so that the cross-section of the tubes alternately decreases and increases, causing blood to flow from the donor to the recipient through the tubes connected to the blood-collecting and infusion needles, and simultaneously causing the medicamental liquid to flow through the tubes having their free ends dipped in the vessel with the medicamental liquid. Thus blood transfusion via one set of tubes is accompanied by the washing of the other set of tubes.

In order to wash the tubes connected to the donor's and recipient's needles, they are replaced by the additional tubes. To this end, the recipient's needle is disconnected from the rubber tube which has been supporting blood flow and connected to the rubber tube earlier immersed at one end in the vessel with the medicamental liquid, and one end of the rubber tube disconnected from the recipient's needle is immersed in said vessel. The cock is set to the other position, ensuring communication of the tube connected to the blood-collecting needle with the tube newly connected to the recipient's needle. Then the direction of rotation of he drum is reversed, and the transfusion procedure carried out, with blood flowing through one set of tubes and the medicamental liquid through the other.

However, apparatus of the above-described type cannot be employed for direct blood transfusion what with the high risk of the donor being infected from the recipient carrying infectious diseases, purulent infection, septic, tuberculous and venerial diseases, malignant neoplasms and malignant blood disorders.

In the above-described apparatus, blood is delivered from the donor to the recipient as a result of mechanical effort exerted on the blood-carrying tubes or directly on the blood flux by the components of the blood-delivery means (pins, rollers, pistons, etc.), partially destroying the formed elements and plasma of the donor's blood, which detracts from the therapeutic potency of the blood, raises its coagulability and susceptibility to clotting.

Such a mechanical effort is likewise liable to damage the tubes wherethrough blood flows, necessitating their frequent replacement, which adversely affects the maintenance aspect.

The means for blood delivery employed in the prior art apparatus require electric motors, mechanical drives or manual efforts on the part of the operators.

Blood transfusion procedures with the use of the prior art apparatus must employ flow meters if the quantity of blood transfused is to be known.

The above two factors add to the design complexity of the apparatus, involve operational difficulties and raise the overall costs.

The prior art apparatus are not amenable to continuous operation, for they require frequent stoppages in order to wash the tubes through which blood flows from the donor to the recipient.

Blood transfusion with the use of the prior art apparatus can be handled by at least two operators, whereas the present invention requires only one person.

In particularly severe cases, prolonged infusion of medicamental liquids to the patients is required. But the prior art apparatus cannot be used for infusing a medicamental liquid prior to and immediately after direct blood transfusion avoiding all manipulations with the recipient's needle associated with the disconnection of the needle from the direct blood transfusion outfit and its connection to the vessel containing the medicamental liquid.

OBJECTS AND SUMMARY OF THE INVENTION

The present invention contemplates providing a direct blood transfusion apparatus permitting direct blood transfusion without any risk of the donor being infected from the recipient to all kinds of patients without exception, whatever type of disease they may have, preserving the formed elements and plasma of the blood and thereby preserving its full therapeutic potency, and which would be simple, reliable and convenient in use requiring the services of not more than one operator.

The foregoing and other objects are attained by the provision of an apparatus for direct blood transfusion, comprising a needle connected to a tube and introduced into the donor's blood system, another needle connected to another tube and introduced into the recipient's blood system, a means of delivering blood to the recipient which so cooperates with said tubes as to ensure blood delivery from the donor to the recipient via said tubes, and a distributing means communicating with said tubes as well as with a vessel containing a medicamental liquid compatible with blood, wherein, in accordance with the invention, the vessel with the medicamental liquid is utilized as a means for delivering blood to the recipient and mounted at a height sufficient to create a hydrostatic head of the medicamental liquid exceeding the blood pressure in the recipient's vasculature, whereas the distributing means mounted below the vessel with the medicamental liquid comprises at least four proportioning vessels vertically mounted in a housing and rigidly coupled therewith, the housing being disposed between an upper disk and a lower disk of a stator in coaxial relationship therewith so as to be able to turn in one direction with respect to the stator, and the upper and lower disks of the stator each have at least four through holes formed therein, and, as the housing turns, each of said proportioning vessels successively passes through at least four positions, in each position being so disposed with respect to the stator that the inlet and outlet thereof register with said holes formed in the stator disks, and the proportioning vessel set to the first position communicates, by way of the inlet thereof, with the hole in the lower disk communicating with the tube connected to the the donor's needle and, by way of the outlet thereof, with the hole formed in the upper disk communicating with the air cushion in the vessel with the medicamental liquid; the proportioning vessel occupying the second position communicates, by way of the inlet thereof, with the hole in the lower disk communication with the tube connected to the recipient's needle; the proportioning vessel occupying the third position communicates, by way of the inlet thereof, with the hole in the lower disk communicating with the vessel with the medicamental liquid; and the inlet of the proportioning vessel occupying the second position and the outlet of the proportioning vessel occupying the third position communicate one with the other via the hole in the upper disk with the aid of a two way cock which, when set to one position corresponding to the blood transfusion process, provides a means of communication of said proportioning vessels one with the other, while set to the other position corresponding to the process of infusion of the medicamental liquid into the recipient's blood system, it connects the proportioning vessel occupying the second position with the vessel with the medicamental liquid; the proportioning vessel occupying the fourth position communicates, by way of the inlet thereof, with the hole in the upper disk communicating with the atmosphere, and, by way of the outlet thereof, with the hole in the lower disk communicating with a vessel for the spent medicamental liquid.

The apparatus of the invention is preferably provided with a dropping-filtering device mounted on the tube connected to the needle introduced into the recipient's blood system, which device, is designed for preventing ingress of air into the recipient's blood system as well as for controlling the rate of transfusion.

The foregoing apparatus offers the following advantages over the prior art units.

Direct blood transfusion to patients by use of the proposed apparatus completely obviates any possibility of the donor getting infected, whatever disease the recipient may be suffering from. The reason for this phenomenon should be sought in the following.

The apparatus guarantees that blood will flow only in one direction, viz. from the donor to the recipient, for the housing can turn only in one direction.

The infection agents from the recipient's blood cannot penetrate the donor's blood system for there are two barriers: first, thay must travel counter to the flow of blood and medicamental liquid and air; secondly between the recipient and the donor the following insulating circuit is provided: the air of the dropping bottle; the donor's blood portion filling the vessel occupying the second position; the air of the latter proportioning vessel; the air of the tubing connecting the vessels in the second and third positions one with the other; the medicamental liquid and air obtaining in the vessel occupying the third position, in the tubing and in the vessel with the medicamental liquid; the air in the vessel with the medicamental liquid and in the tube connecting this vessel with the proportioning vessel occupying the first position.

The proposed apparatus obviates all risk of the formed elements and plasma of the donor's blood sustaining any mechanical damage, for the blood flowing from the donor to the recipient experiences no mechanical effort and is in contact solely with air. Hence, the blood transfused to the recipient loses none of its therapeutic properies.

The design of the proposed apparatus is such as to permit simultaneously and continuously drawing blood from the donor into one proportioning vessel and delivering it to the recipient from another proportioning vessel, with the two other blood-free proportioning vessels being simultaneously washed.

The proposed apparatus allows of an extremely simple process of infusion of medicamental liquids into the recipient's blood system, requiring no manipulations of the recipient's needle. To this end, the two-way cock is set to the position for connecting the vessel containing the medicamental liquid, e.g. physiological solution, with the proportioning vessel occupying the second position, so that the medicamental liquid is delivered from the latter proportioning vessel via the dropping bottle, the tube and the needle to the recipient.

The blood transfusion procedure by use of the proposed apparatus can be carried out by a single physician who only has to watch how blood fills the proportioning vessel communicating with the collecting needle and how blood is forced out of the proportioning vessel and into the infusion needle; he must also see to it that the housing is timely turned. It follows from the above that the proposed apparatus is extremely simple in handling.

Monitoring the quantity of blood transfused in the proposed apparatus requires no special meters, for it can be registered either by the amount of blood collected from the donor into the graduated proportioning vessel, or by the quantity of medicamental liquid flowing out of the vessel with the medicamental liquid, likewise graduated.

The proposed apparatus incorporates no electric motors or mechanical drives which are needed in the prior art units for delivering blood from the donor to the recipient. In the proposed apparatus, the force driving the blood from the donor to the recipient is created by the hydrostatic head of a medicamental liquid compatible with blood which is contained in a vessel disposed at a certain height with respect to the recipient.

The apparatus of the present invention is portable, simple in design and reliable in operation, which renders it usable for blood transfusion in any conditions.

BRIEF DESCRIPTION OF THE DRAWINGS

Other objects and advantages of the present invention will be appreciated from the following detailed description of several exemplary embodiments thereof taken in conjunction with the accompanying drawings, wherein:

FIG. 3 illustrates a locking mechanism preventing reverse rotation of the housing, in accordance with invention;

FIG. 4 is a view taken on the line IV—IV in FIG. 3;

DETAILED DESCRIPTION OF THE PREFERRED EMBODIMENT

Figure 1:
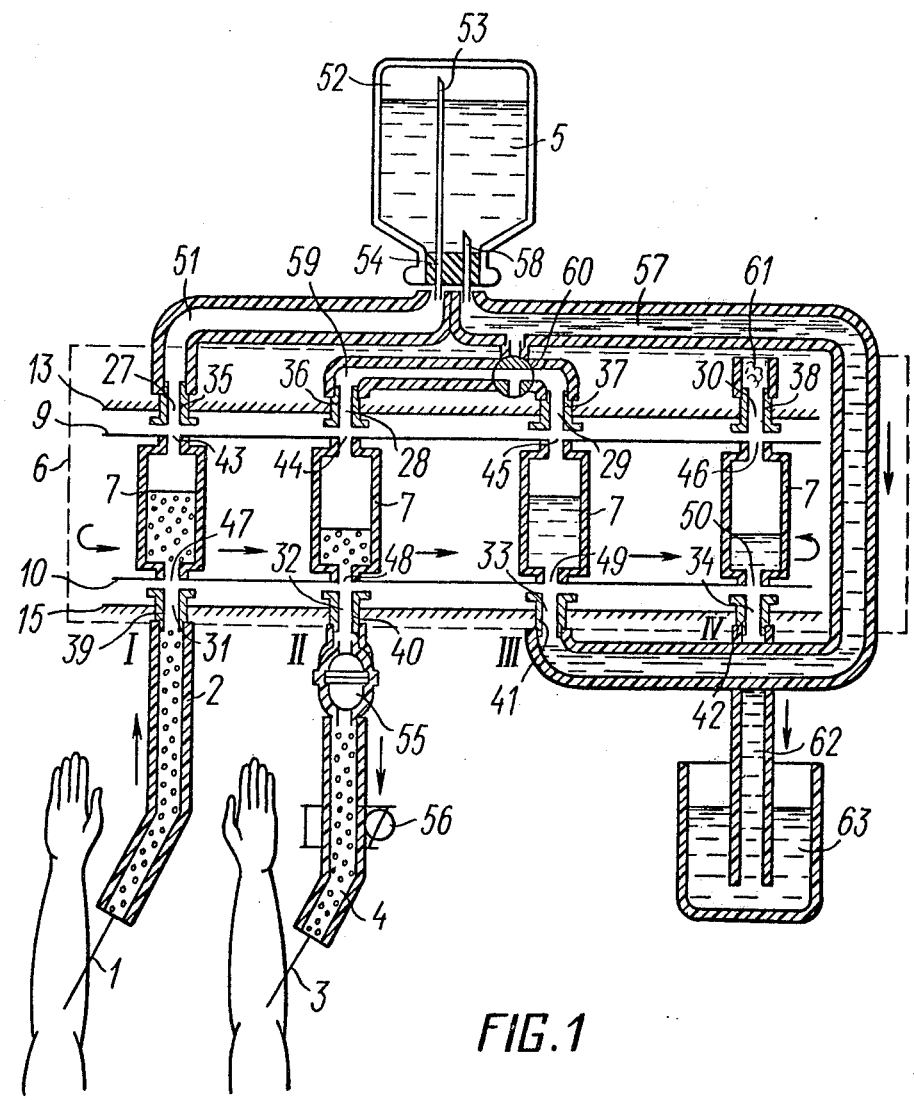
FIG. 1 is a schematic representation of an apparatus for direct blood transfusion, in accordance with the invention.

Referring now to the drawings, the proposed apparatus for direct blood transfusion comprises a needle 1 (FIG. 1) for collecting blood from the donor which is connected to a tube 2, and a needle 3 for infusing the collected blood to the recipient connected to a tube 4, the tubes 2 and 4 being constructed from a transparent polymeric material. A vessel 5 containing a medicamental liquid compatible with blood, e.g. physiological solution, serves as a means for delivering blood from the donor to the recipient, as the vessel 5 is disposed at a certain height with respect to the recipient's position which creates a hydrostatic head of the medicamental liquid exceeding the blood pressure in the recipient's vasculature. The walls of the vessel 5 are graduated, so that the quantity of the outflowing liquid, and hence the quantity of blood transfused, can be monitored thereby.

The apparatus is provided with a distributing means 6 installed below the vessel 5. The distributing means 6 is composed of four proportioning vessels 7 constructed from a transparent polymeric material. The walls of the proportioning vessels 7 are graduated, allowing the quantity of blood transfused to be monitored. The proportioning vessels 7 are vertically mounted in a housing 8 (FIG. 2) and rigidly coupled therewith. The housing 8 is built around an upper disk 9 and a lower disk 10 interconnected by means of a vertical tube 11. The disks 9 and 10 are each provided with four lugs 12 disposed at equal intervals about the circumference of the disks 9 and 10. The proportioning vessels 7 are fitted on the lugs 12. Thus is provided a compact arrangement and rigid coupling of the proportioning vessels 7 to the housing 8.

The housing 8 is disposed between an upper disk 13 of a stator 14 and a lower disk 15 of the stator 14 in coaxial relationship therewith. The housing 8 is loosely fitted on an axle 16 so as to be able to turn in one direction with respect to the stator 14. While turning, the housing 8 occupies four successive positions. The housing 8 is turned with the aid of a handle 17 likewise loosely fitted on the axle 16 which can be set to two extreme positions. The ability of the housing 8 to turn in one direction only is provided for by a locking mechanism preventing the housing 8 from reverse rotation. Said mechanism is formed as an end-mounted ratchet mechanism 18 (FIG. 3) which comprises a ratchet wheel composed of four teeth 19 formed on the outer surface of the lower disk 10 of the housing 8. The handle 17 is provided with a pin 20 resting on a spring 21. The spring 21 is fastened to the handle 17 with bolts 22. In the lower disk 15 there is formed a slot 23 (FIG. 4) wherein the pin 20 moves therealong as the handle 17 is turned.

The lower disk 15 and the upper disk 13 (FIG. 2) of the stator 14 are loose-fitted on the axle 16 without freedom to turn thereabout. The upper disk 13 mounts a spring lock 24 urging the disks 9 and 10 of the housing 8 against the disks 13 and 15, respectively, of the stator 14. The spring lock 24 is held on the axle 16 by means of a pin 25.

The axle 16 is mounted on a screw clamp 26, the latter being designed to fasten the distributing means 6 onto a bearing surface (not shown in the drawings).

Figure 5:
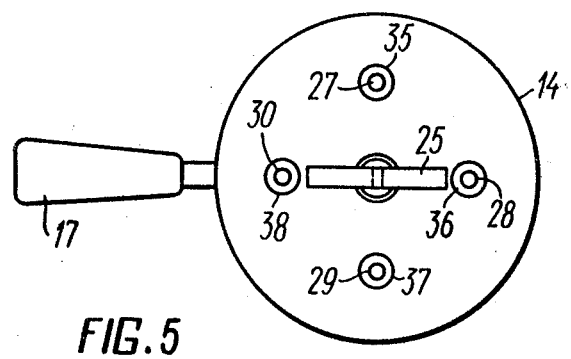
FIG. 5 is a plan view of a distributing means, in accordance with the invention.

The upper disk 13 of the stator 14 and the lower disk 15 of the stator 14 each have four through holes 27, 28, 29 and 30 (FIG. 5) and 31, 32, 33 and 34 (FIG. 1), respectively, uniformly arranged about the circumference of the disks 13 and 15, respectively. Connecting branches 35, 36, 37, 38, 39, 40, 41 and 42 are coupled to the holes 27, 28, 29, 30, 31, 32, 33 and 34, respectively.

The disks 9 and 10 of the housing 8 also have holes 43, 44, 45 and 46 and 47, 48, 49 and 50, respectively, uniformly arranged about the circumference of the disks 9 and 10, respectively. These holes 43, 44, 45, 46, 47, 48, 49 and 50 are the inlets and the outlets of the proportioning vessels 7.

As the housing 8 turns, each of said proportioning vessels 7 successively passes through four positions I, II, III and IV (FIG. 1). In each of the above positions, the vessels 7 are so positioned with respect to the stator 14 that the inlet and the outlet thereof register with said holes 27, 28, 29, 30, 31, 32, 33 and 34 of the stator 14.

The proportioning vessel 7 occupying the first position (I) communicates, by way of the inlet thereof, with the tube 2 connected to the blood-collecting needle 1 via the hole 31 and the connecting branch 39. The outlet of the vessel 7 communicates, via the hole 27, the connecting branch 35 and a tubing 51, with an air cushion 52 of the vessel 5 containing the medicamental liquid. This accomplished by a needle 53 which is coupled to the tubing 51 and inserted into the vessel 5 above the level of the medicamental liquid. The needle 53 enters the vessel 5 through a cork seal 54 which prevents the medicamental liquid from leaking out of the vessel 5.

The proportioning vessel 7 occupying the second position (II) communicates, by way of the outlet thereof, with the tube 4 connected to the needle 5 introduced into the recipient's blood system via the hole 32 and the connecting branch 40. The tube 4 is provided with a dropping-filtering device comprising a dropping bottle 55 with a filter and a clamp 56. The dropping bottle 55 is designed to prevent ingress of air into the recipient's blood system as well as for counting the number of drips. The clamp 56 serves for controlling the rate of blood transfusion. Both the dropping bottle 55 and the clamp 56 are of a known design.

The proportioning vessel 7 occupying the third position (III) communicates, by way of the inlet thereof, with the vessel 5 containing the medicamental liquid via the hole 33, the connecting branch 41 and a tubing 57. The tubing 57 carries a needle 58 on the end thereof. The needle 58 is introduced into the vessel 5 through the seal 54 below the level of the medicamental liquid. The outlet of the vessel 7 occupying the third position communicates with the inlet of the vessel 7 occupying the second position (II) via the holes 28 and 29 as well as via the connecting branches 36 and 37 by means of a tubing 59 which mounts a two-way cock 60. Set to one of its positions (shown in FIG. 1) corresponding to the blood transfusion process, the cock 60 interconnectes the above-described proportioning vessels 7. Set to the other position corresponding to the infusion of the medicamental liquid into the recipient's blood system, the cock 60 interconnects the proportioning vessel 7 occupying the second position (II) and the vessel 5 with the medicamental liquid via the hole 28, the connecting branch 36 and the tubings 59 and 57.

The proportioning vessel 7 occupying the fourth position (IV) communicates, via the hole 30 and the connecting branch 38, with the atmosphere. A bactericidal filter 61 is fitted into the connecting branch 38 to prevent air-borne infection agents from finding ingress into this vessel 7. The outlet of said vessel 7 communicates, via the hole 34, the connecting branch 42 and a tubing 62, with a vessel 63 for the spent medicamental liquid.

The proposed apparatus operates in the following manner.

Prior to direct blood transfusion from the donor to the recipient, a medicamental liquid is infused into the latter's blood system.

To this end, the following operations are carried out.

The two-way cock 60 (FIG. 1) is set to a position (not shown in the drawing) for interconnecting the vessel 5 with the medicamental liquid and the proportioning vessel 7 occupying the second position (II) via the tubings 57 and 59 as well as the connecting branch 36.

The needle 3 introduced into the recipient's blood system together with the tube 4 is lifted to a certain height, and the dropping bottle 55 is turned to be filled with the medicamental liquid arriving from the vessel 5 via the needle 58, the tubing 57, the cock 60, the tubing 59, the connecting branch 36, the proportioning vessel 7 occupying the second position (II), the connecting branch 40 and the tube 4. The level of the medicamental liquid in the dropping bottle 55 must be such as to obviate ingress of air into the recipient's blood system.

Having been filled to a predetermined level, the dropping bottle 55 is set to the working position. Then a small quantity of the medicamental liquid is allowed to flow out of the vessel 5 until it squirts from the needle 3, after which the needle 3 is introduced into the recipient's blood system. By adjusting the clamp 56, the drop-infusion of the medicamental liquid to the recipient is ensured. Then the needle 1 is introduced into the donor's blood system, and the clamp 56 is fully opened. This will cause the medicamental liquid to flow from the vessel 5 via the tubbing 57 and the connecting branch 36 to the vessel 7 occupying the second positioin (II). From this vessel 7 the medicamental liquid will flow through the connecting branch 40, the dropping bottle 55, the tube 4 and the needle 3 into the blood system of the recipient. The flow of the medicamental liquid from the vessel 5 and into the recipient's blood system in the above-described way is ensured by lifting the vessel 5 to a height sufficient to create a hydrostatic head of the medicamental liquid exceeding the blood pressure in the recipient's vasculature.

As the liquid flows from the vessel 5 and into the recipient's blood system, a vacuum will be created in the upper portion of the vessel 5, owing to which the blood freely flowing from the donor's vessel is drawn in through the tube 2 and via the connecting branch 39 into the proportioning vessel 7 occupying the first position (I). As soon as this proportioning vessel 7 is filled with the donor's blood, the housing 8 (FIG. 3) is turned through 90° by manipulating the handle 17 in an appropriate manner.

The housing 8 is turned as follows.

First, the handle 17 is turned in a direction opposite to the direction of movement of the housing 8, with the pin 20 displacing along the slot 23 (FIG. 4) formed in the lower disk 15 of the stator 14 (FIG. 3) and sliding about the inclined surface of the tooth 19 formed on the lower disk 10 of the housing 8. When the handle 17 reaches its extreme position, the pin 20 passes along the vertical surface of the tooth 19, engaging the latter.

Then the handle 17 is turned in the direction of movement of the housing 8 corresponding to the movement toward the recipient of the vessel 7 (FIG. 1) occupying the first position (I) and now filled with the donor's blood. Since the pin 20 secured to the handle 17 engages the tooth 19 provided on the lower disk 10 of the housing 8, the housing 8 turns together with the handle 17 (FIG. 3). With the handle 17 set to its extreme position, the pin 20 rests against the edge of the slot 23, and the holes 27 (FIG. 1), 28, 29 and 30 of the upper disk 13 of the stator 14 register with the holes 43, 44, 45 and 46 of the upper disk 9 of the housing 8, while the holes 31, 32, 33 and 34 of the lower disk 15 of the stator 14 register with the holes 47, 48, 49 and 50 of the lower disk 10 of the housing 8, so that the inlets and outlets of the proportioning vessels 7 are aligned opposite said holes 27, 28, 29, 30, 31, 32, 33 and 34 of the stator 14.

Figure 2:
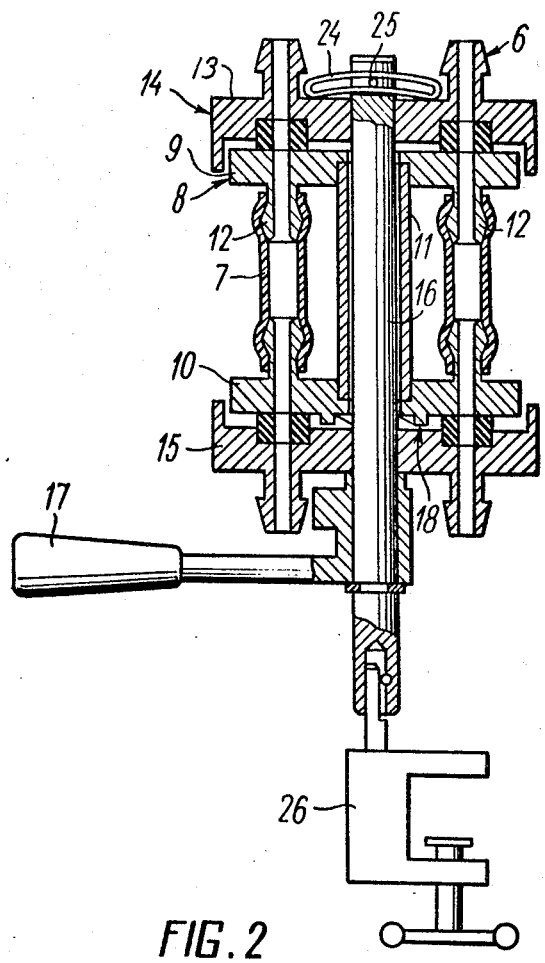
FIG. 2 is a distributing means, in accordance with the invention, in longitudinal section.

As the housing 8 is turned through 90°, the proportioning vessels 7 occupying the first, second, third and fourth positions (I, II, III and IV) are respectively moved to the second, third, fourth and first positions (II, III, IV and I). The cock 60 is set to the position shown in FIG. 1 to interconnect the proportioning vessels 7 occupying the second and third positions (II and III), putting the process of direct blood transfusion underway. The following processes will take place in the proportioning vessels 7 occupying the first, second, third and fourth positions (I, II, III and I) in each of the four positions of the housing 8 (FIG. 2).

The proportioning vessel 7 (FIG. 1) occupying the first position (I) is filled with the donor's blood, as described hereabove.

From the vessel 5 the medicamental liquid flows via the needle 58, the tubing 57 and the connecting branch 41 into the proportioning vessel 7 occupying the third position (III), ousting the air from this vessel 7. The ousted air is supplied via the connecting branch 37, the cock 60, the tubing 59 and the connecting branch 36 to the proportioning vessel 7 occupying the second position (II), forcing therefrom the donor's blood supplied thereinto in the previous, i.e. first, position (I). The donor's blood thus forced out of the vessel 7 flows through the connecting branch 40, the dropping bottle 55, the tube 4 and the needle 3 into the recipient's blood system.

The proportioning vessel 7 occupying the third position (III) is filled with the medicamental liquid, as described hereabove. From the proportioning vessel 7 occupying the fourth position (IV) the medicamental liquid which has filled this vessel 7 in the previous, e.g. third, position (III) is drained via the connecting branch 42 and the tubing 62 into the vessel 36 for the spent medicamental liquid.

Thus, as the housing 8 (FIG. 2) turns, each of the proportioning vessels 7 successively passes through four positions. In the first position (I) (FIG. 1), each proportioning vessel 7 is filled with the donor's blood; in the second position, is emptied of the blood which is delivered to the recipient; in the third position, is filled with the medicamental liquid, thereby being washed; and in the fourth position, is emptied of the spent medicamental liquid, thus becoming clean and ready for being again filled with the donor's blood.

It is clear from the above that the distributing means 6 of the proposed apparatus permits effecting the processes of direct blood transfusion and washing of the vessels 7 being filled with that blood in a continuous manner and simultaneously; the foregoing design further absolutely prevents accidental infection of the donor. Of course, the housing of the apparatus may be turned automatically.

The above-described means for delivering blood employed in the proposed apparatus enables blood to be delivered avoiding any mechanical action on the blood flow. As can be seen from the description of the apparatus operation, the blood flow is in contact with air alone on its way from the donor to the recipient, so that the donor's blood has all its therepeutic properties unimpaired for the formed elements and plasma of the blood are preserved from destruction.

After the direct blood transfusion process is over, the medicamental liquid is again infused into the recipient's blood system, the apparatus operating as follows.

The needle 1 is withdrawn from the donor's blood system and immersed in a vessel (not shown in the drawings) containing a medicamental liquid compatible with blood, the remainder of the blood in the tube 2 connected to the needle 1 introduced into the donor's blood system being delivered together with the medicamental liquid into the proportioning vessel 7 occupying the first position (I). After this vessel 7 has been filled with the medicamental liquid, the housing 8 (FIG. 2) is turned through 90°, causing the medicamental liquid together with the remainder of the blood to be forced out of this vessel 7, now occupying the second position (II), into the recipient's blood system in a manner already described hereabove.

Then the needle 1 is withdrawn from the above-described vessel (not shown in the drawings), and the cock 60 is set to the position (not shown in FIG. 1) for intercounecting the vessel 5 containing the medicamental liquid and the proportioning vessel 7 occupying the second position (II). The clamp 56 is manipulated to ensure drop-infusion of the medicamental liquid into the blood system of the recipient.

From the above it follows that the proposed apparatus permits medicamental liquids to be infused into the recipient's blood system prior to and following direct blood transfusion in an extremely simple way, avoiding all manipulations of the needle 3 introduced into the recipient's blood system.

The proposed apparatus is simple and compact in design and reliable in operation. It requires no special meters to determine the quantity of blood transfused, nor electric motors or mechanical drives for blood delivery. The proposed apparatus can easily be handled by a single person under any conditions.

What is claimed is:

1. An apparatus for direct blood transfusion from a donor to a recipient, comprising: a needle for introduction into the donor's blood system; a tube connected to said needle; a second needle for introduction into the recipient's blood system; a second tube connected to said second needle; a vessel filled with a medicamental liquid compatible with blood in such a way as to leave an air space forming an air cushion in said vessel, said vessel being lifted to a height sufficient for creating a hydrostatic head of the medicamental liquid exceeding the blood pressure in the recipient's vasculature, whereby said head functions as a means for delivering blood to the recipient via said tubes; a second vessel for collecting the spent medicamental liquid; a distributing means mounted on said vessel with the medicamental liquid; a two-way cock of said distributing means; a stator of said distributing means; an upper disk of said stator; a lower disk of said stator; each disk of said stator having at least four through holes, the first hole of said upper disk communicating with said vessel with the medicamental liquid, whereas the respective first hole of said lower disk communicates with said tube connected to said needle introduced into the donor's blood system, the second hole of said upper disk communicates with the third hole formed in that same disk via said two-way cock, the respective second hole formed in the lower disk communicates with said second tube connected to said second needle introduced into the recipient's blood system, the respective third hole formed in said lower disk communicates with said vessel with the medicamental liquid, the fourth hole formed in said upper disk communicates with the atmosphere, while the respective fourth hole formed in said lower disk communicates with said second vessel with the spent medicamental liquid; a housing of said distributing means disposed between said upper and lower disks of said stator in coaxial relationship therewith; four proportioning vessels of said distributing means vertically mounted in said housing and rigidly coupled therewith; an inlet and an outlet of each of said proportioning vessels; said housing rotatable in one direction with respect to said stator which, while turning, ensures that each of said proportioning vessels successively passes through four positions, being so disposed in each of said positions with respect to said stator that said inlet and outlet of each of said proportioning vessels are positioned opposite said holes formed in said upper and lower disks of said stator, said proportioning vessel occupying said first position has said inlet thereof communicating with said first hole of said lower disk, said proportioning vessel occupying said second position has said inlet thereof communicating with said second hole formed in said lower disk, said proportioning vessel occupying said third position has said inlet thereof communicating with said third hole formed in said lower disk, said inlet of said proportioning vessel occupying said second position and said outlet of said proportioning vessel occupying said third position communicating one with the other by way of said appropriate second and third holes formed in said upper disk with the aid of said two-way cock, said two-way cock, when set to one position corresponding to the process of blood transfusion, connecting said porportioning vessels one with the other, whereas, when set to the other position corresponding to recipient's blood system said two-way cock connects said proportioning vessel occupying said second position with said vessel with the medicamental liquid, and said proportioning vessel occupying said fourth position has said inlet thereof communicating with said fourth hole formed in said upper disk, said outlet of said fourth proportioning vessel communicating with said fourth hole formed in said lower disk.

2. The apparatus as set forth in claim 1, further comprising a dropping-filtering device mounted on said second tube connected to said second needle introduced into the recipient's blood system, said dropping-filtering device being designed for preventing ingress of air into the recipient's blood system as well as for controlling the rate of blood transfusion.

3. The apparatus of claim 1, wherein said tube, said second tube, and said four proportioning vessels are made of a transparent polymeric material.

4. The apparatus of claim 1, wherein said vessel filled with a medicamental liquid and said four proportioning vessels are graduated.

\* \* \* \* \*